United States Patent
Konstantino

(10) Patent No.: US 7,513,886 B2
(45) Date of Patent: Apr. 7, 2009

(54) FACILITATED BALLOON CATHETER EXCHANGE

(75) Inventor: Eitan Konstantino, Orinda, CA (US)

(73) Assignee: Angioscore, Inc., Fremont, CA (US)

( * ) Notice: Subject to any disclaimer, the term of this patent is extended or adjusted under 35 U.S.C. 154(b) by 414 days.

(21) Appl. No.: 11/397,583

(22) Filed: Apr. 3, 2006

(65) Prior Publication Data

US 2006/0259062 A1 Nov. 16, 2006

Related U.S. Application Data

(63) Continuation of application No. PCT/US2004/041877, filed on Dec. 8, 2004, which is a continuation-in-part of application No. 10/775,357, filed on Feb. 9, 2004, now Pat. No. 7,022,104.

(60) Provisional application No. 60/528,263, filed on Dec. 8, 2003.

(51) Int. Cl.
A61M 29/00 (2006.01)
A61M 31/00 (2006.01)
A61M 37/00 (2006.01)

(52) U.S. Cl. .......................... 604/102.02; 604/102.01; 604/103.06; 604/103.08

(58) Field of Classification Search ............ 604/102.02, 604/103.04, 103.08, 102.01, 103.06, 96.01, 604/915–916, 921; 606/191–192, 194
See application file for complete search history.

(56) References Cited

U.S. PATENT DOCUMENTS

| 4,748,982 A | 6/1988 | Horzewski et al. |
| 4,762,100 A | 8/1988 | Kowal |
| 4,762,129 A | 8/1988 | Bonzel |
| 4,947,864 A | 8/1990 | Shockey et al. |
| 4,988,356 A | 1/1991 | Crittenden et al. |
| 5,048,548 A | 9/1991 | Ramsey, Jr. |
| 5,049,131 A | 9/1991 | Deuss |
| 5,061,273 A | 10/1991 | Yock |
| 5,135,535 A | 8/1992 | Kramer |
| 5,156,594 A | 10/1992 | Keith |
| 5,180,367 A | 1/1993 | Kontos et al. |
| 5,195,978 A | 3/1993 | Schiffer |
| 5,232,445 A | 8/1993 | Bonzel |
| 5,263,963 A | 11/1993 | Garrison et al. |
| 5,281,203 A | 1/1994 | Ressemann |
| 5,300,085 A | 4/1994 | Yock |
| 5,328,472 A | 7/1994 | Steinke et al. |
| 5,334,147 A | 8/1994 | Johnson |
| 5,336,184 A | 8/1994 | Teirstein |
| 5,346,505 A | 9/1994 | Leopold |
| 5,350,395 A | 9/1994 | Yock |
| 5,364,376 A | 11/1994 | Horzewski et al. |
| 5,370,616 A | 12/1994 | Keith et al. |

(Continued)

FOREIGN PATENT DOCUMENTS

WO    WO 97/07756    3/1997

(Continued)

*Primary Examiner*—Manuel A Mendez
(74) *Attorney, Agent, or Firm*—Townsend and Townsend and Crew LLP

(57) ABSTRACT

A balloon catheter comprises a catheter body, a balloon at a distal end of the catheter body, and a guidewire tube within the balloon and separate from the catheter body. A catheter may be introduced over a guidewire by passing the guidewire through a guidewire lumen in the guidewire tube. No guidewire lumen is provided within the catheter body.

27 Claims, 6 Drawing Sheets

U.S. PATENT DOCUMENTS

| | | | |
|---|---|---|---|
| 5,380,283 A | 1/1995 | Johnson |
| 5,383,853 A | 1/1995 | Jung et al. |
| 5,395,335 A | 3/1995 | Jang |
| 5,413,559 A | 5/1995 | Sirhan et al. |
| 5,415,639 A | 5/1995 | VandenEinde et al. |
| 5,443,457 A | 8/1995 | Ginn et al. |
| 5,451,223 A | 9/1995 | Ben-Simhon |
| 5,458,613 A | 10/1995 | Gharibadeh et al. |
| 5,460,185 A | 10/1995 | Johnson et al. |
| 5,468,225 A | 11/1995 | Teirstein |
| 5,472,425 A | 12/1995 | Teirstein |
| 5,496,600 A | 3/1996 | Peiffer et al. |
| 5,501,227 A | 3/1996 | Yock |
| 5,531,690 A | 7/1996 | Solar |
| 5,545,134 A | 8/1996 | Hilaire et al. |
| 5,554,118 A | 9/1996 | Jang |
| 5,571,094 A | 11/1996 | Sirhan |
| 5,607,406 A | 3/1997 | Hernandez et al. |
| 5,620,417 A | 4/1997 | Jang et al. |
| 5,626,600 A | 5/1997 | Horzewski et al. |
| 5,685,312 A | 11/1997 | Yock |
| 5,709,658 A | 1/1998 | Sirhan et al. |
| 5,728,067 A | 3/1998 | Enger |
| 5,738,667 A | 4/1998 | Solar |
| 5,749,888 A | 5/1998 | Yock |
| 5,769,868 A | 6/1998 | Yock |
| 5,776,191 A | 7/1998 | Mazzocco |
| 5,807,355 A | 9/1998 | Ramzipoor et al. |
| 5,810,869 A | 9/1998 | Kaplan et al. |
| 5,814,061 A | 9/1998 | Osborne et al. |
| 5,827,241 A | 10/1998 | Douk et al. |
| 5,830,227 A | 11/1998 | Fischell et al. |
| 5,833,659 A | 11/1998 | Kranys |
| 5,846,246 A | 12/1998 | Dirks et al. |
| 5,855,685 A | 1/1999 | Tobe et al. |
| 5,891,056 A | 4/1999 | Ramzipoor |
| 5,919,164 A | 7/1999 | Andersen |
| 5,919,175 A | 7/1999 | Sirhan |
| 5,921,971 A | 7/1999 | Agro et al. |
| 5,935,114 A | 8/1999 | Jang et al. |
| 5,947,927 A | 9/1999 | Mertens |
| 5,980,484 A | 11/1999 | Ressemann et al. |
| 5,980,486 A | 11/1999 | Enger |
| 6,007,517 A | 12/1999 | Anderson |
| 6,027,475 A | 2/2000 | Sirhan et al. |
| 6,036,715 A | 3/2000 | Yock |
| 6,056,722 A | 5/2000 | Jayaraman |
| 6,129,706 A | 10/2000 | Janacek |
| 6,129,708 A | 10/2000 | Enger |
| 6,165,197 A | 12/2000 | Yock |
| 6,248,092 B1 | 6/2001 | Miraki et al. |
| 6,273,879 B1 | 8/2001 | Keith et al. |
| 6,277,093 B1 | 8/2001 | Lee |
| 6,361,529 B1 | 3/2002 | Goodin et al. |
| 6,478,807 B1 | 11/2002 | Foreman et al. |
| 6,485,457 B1 | 11/2002 | Hisamatsu et al. |
| 6,527,789 B1 | 3/2003 | Lau et al. |
| 6,533,754 B1 | 3/2003 | Hisamatsu et al. |
| 6,569,180 B1 | 5/2003 | Sirhan et al. |
| 6,585,657 B2 | 7/2003 | Yock |
| 6,605,057 B2 | 8/2003 | Fitzmaurice et al. |
| 6,960,186 B1 | 11/2005 | Fukaya et al. |
| 7,022,104 B2 * | 4/2006 | Konstantino ........... 604/102.02 |
| 2002/0004053 A1 | 1/2002 | Biel |
| 2003/0012301 A1 | 1/2003 | Walker |
| 2003/0208221 A1 | 11/2003 | El-Nounou |
| 2004/0267196 A1 | 12/2004 | Miki et al. |
| 2006/0149308 A1 | 7/2006 | Melsheimer et al. |

FOREIGN PATENT DOCUMENTS

| | | |
|---|---|---|
| WO | WO 99/13935 | 3/1999 |

* cited by examiner

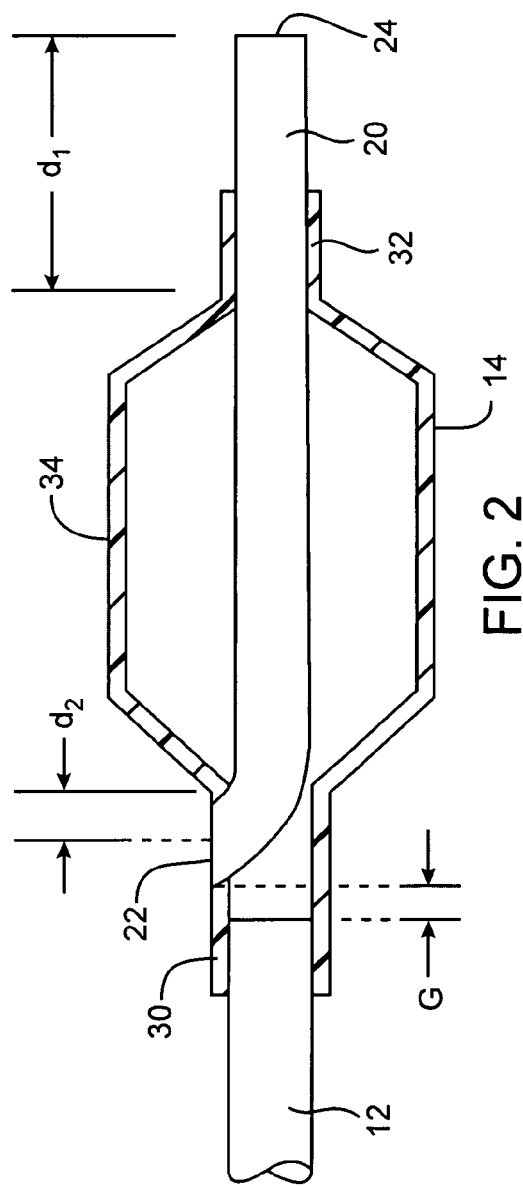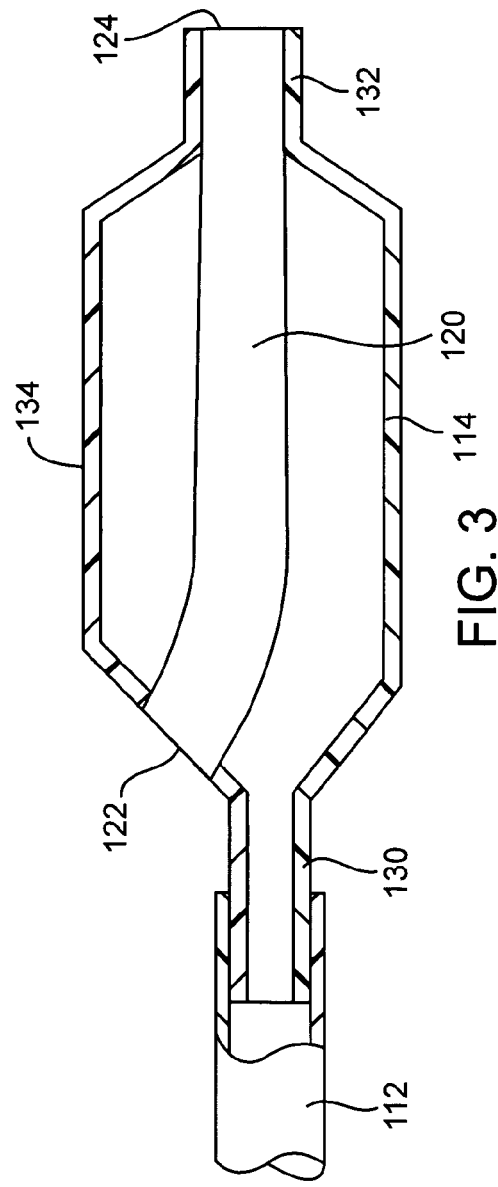

FACILITATED BALLOON CATHETER EXCHANGE

CROSS-REFERENCES TO RELATED APPLICATIONS

The present application is a continuation of PCT/US2004/041877, filed on Dec. 8, 2004, which was a continuation-in-part of U.S. patent application Ser. No. 10/775,357, filed on Feb. 9, 2004 (now U.S. Pat. No. 7,022,104), which claimed the benefit of U.S. Provisional Patent Application Ser. No. 60/528,263, filed on Dec. 8, 2003, the full disclosures of which are incorporated herein by reference.

BACKGROUND OF THE INVENTION

1. Field of the Invention

The present invention relates generally to medical apparatus and methods. More particularly, the present invention relates to catheters having guide wire tubes disposed within expandable structures for facilitating catheter exchange over a guide wire.

Percutaneous transluminal angioplasty procedures have become a therapy of choice for treating stenosed regions in the patient's vasculature, particularly the coronary vasculature. Recently, the use of such angioplasty procedures has often been combined with stent placement and/or radiation treatment to inhibit restenosis and hyperplasia following angioplasty. When performing such multiple, sequential treatments, it is usually necessary to "exchange" catheters which are used to perform each of the procedures. That is, the initial angioplasty treatment will be performed using a balloon angioplasty catheter. After the angioplasty is completed, a second catheter carrying a stent or other vascular prosthesis must then be introduced to the treatment site. Introduction of the second catheter involves first removing the balloon angioplasty catheter and then placing the second catheter in the treatment region. Optionally, a third catheter may then be exchanged for the second in order to perform radiation or other treatments in order to inhibit hyperplasia.

In performing such multiple, sequential treatments, most physicians prefer to leave a "guidewire" in place to the treatment location. A guidewire is a small diameter, highly flexible wire that can be steered to the target location through the vasculature and which then acts as a guide path for introducing and positioning the balloon angioplasty and other interventional catheters.

In the early days, balloon angioplasty catheters were designed to be introduced into the vasculature in an "over-the-wire" manner. That is, the catheters were designed to have passages, commonly referred to as guidewire lumens, which extended the entire distance from the distal end of the catheter to the proximal end of the catheter. The catheter could then be loaded over a proximal end of a guidewire which was already in place in the patient and then advanced over the guidewire until a distal end of the catheter reached the target site. While functional, the need to maintain control of the guidewire while the interventional catheter was being introduced meant that the guidewire had to have an excess length outside of the patient which was greater than the length of the catheter being introduced. If the length were any shorter, the treating physician would not be able to hold on to the guidewire as the catheter was being introduced. Although necessary for catheter introduction, the excess guidewire length (optionally in the form of a detachable extension) was very difficult to manage during other parts of the treatment.

To overcome the difficulties associated with very long guidewires "rapid exchange" or "monorail" balloon angioplasty catheters were developed. A number of specific designs have been developed over the years, and the rapid exchange catheters generally have a shortened guidewire lumen which extends from a distal tip of the catheter to an exit port located closer to the distal end of the catheter than to the proximal end. By reducing the length of the guidewire lumen, the need for a guidewire having excess length outside of the patient is also reduced.

The use of rapid exchange catheters has become wide spread, and they have proven to be particularly valuable for use as stent delivery catheters. Stent delivery catheters are normally used after an initial angioplasty treatment. In such cases, the angioplasty catheter will be removed and exchanged for the stent delivery catheter. Use of an angioplasty catheter having a rapid exchange design facilitates removal of the angioplasty catheter over short guidewires. Similarly, use of the stent delivery catheter having a rapid exchange design facilitates introduction of the catheter over the guidewire which remains in place in the patient.

Most rapid exchange balloon angioplasty catheters have one of two basic designs. The first design was disclosed initially in U.S. Pat. No. 4,762,100 to Bonzel. In the Bonzel design, an angioplasty balloon catheter having a balloon at the distal end of the shaft is provided with a second guidewire tube positioned through the balloon in parallel with the distal tip of the shaft. While functional, this design adds to both the diameter and stiffness of the distal tip of the shaft, both of which properties make it more difficult to introduce the catheter to narrow regions of the coronary and other vasculature. The second general design was first disclosed in U.S. Pat. No. 5,048,548 to Yock et al. In the Yock design, the shaft of an angioplasty catheter is provided with at least two lumens, a balloon inflation lumen and a distal guidewire lumen. Usually, the two lumens are disposed in parallel over at least a portion of the length of the catheter body, again increasing the diameter and potential of the stiffness of the catheter. Moreover, the provision of a "notch" or hole in the side of the catheter body can cause the body to kink when delivered under certain conditions.

For these reasons, it would desirable to provide improved and alternative apparatus, methods, kits, and the like for permitting the exchange of catheters over guidewires in a "rapid exchange" or other facilitated manner. It would be particularly desirable to provide improved balloon angioplasty and other catheters which can be introduced over a shortened guidewire without the need to provide a guidewire lumen anywhere in the catheter body and/or to provide a separate guidewire tube in parallel with or overlapping with the catheter body. Such designs should be compatible with catheters having very low profile distal ends, i.e., diameters of 5 Fr, 4 Fr, and even below, at their distal ends. At least some of these objectives will be met by the invention described and claimed hereinafter.

2. Description of Background Art

Rapid exchange catheters having guidewire exchange devices are described in U.S. Pat. Nos. 5,281,203; 5,571,094; and 5,919,175. Sleeves for positioning stents, drug infusion tubes, imaging transducers, and other interventional devices over balloon angioplasty catheters are described in U.S. Pat. Nos. 5,776,191; 5,810,869; and PCT Publication W097/07756. Rapid exchange and related catheters are described in U.S. Pat. Nos. 6,605,057; 6,533,754; 6,527,789; 6,569,180; 6,585,657; 6,478,807; 6,361,529; 6,277,093; 6,273,879; 6,248,092; 6,165,197; 6,129,708; 6,036,715; 6,056,722; 6,027,475; 6,007,517; 5,980,486; 5,980,484; 5,947,927;

5,921,971; 5,935,114; 5,919,164; 5,891,056; 5,855,685; 5,846,246; 5,833,659; 5,830,227; 5,827,241; 5,807,355; 5,814,061; 5,769,868; 5,749,888; 5,738,667; 5,728,067; 5,709,658; 5,685,312; 5,626,600; 5,620,417; 5,607,406; 5,554,118; 5,545,134; 5,531,690; 5,501,227; 5,496,600; 5,472,425; 5,468,225; 5,460,185; 5,458,613; 5,451,223; 5,443,457; 5,415,639; 5,413,559; 5,395,335; 5,383,853; 5,364,376; 5,350,395; 5,346,505; 5,336,184; 5,334,147; 5,328,472; 5,300,085; 5,380,283; 5,281,203; 5,263,963; 5,232,445; 5,195,978; 5,135,535; 5,061,273; 5,048,548; 4,762,129; 4,988,356; 4,947,864; 4,762,100; 4,748,982; US2003/0208221; US2003/012301; US 2002/0004053; and WO 99/13935.

BRIEF SUMMARY OF THE INVENTION

The present invention provides improved balloon and other interventional and diagnostic catheters which are adapted for facilitated exchange over guidewires. The catheters comprise both a catheter body and a separate guidewire tube, where the catheter body has at least a balloon inflation lumen and the guidewire tube has a guidewire lumen. The catheter body and the guidewire tube are not directly connected, and an axial gap will usually be present between a distal end of the catheter and a proximal end of the guidewire tube. Usually, the guidewire will pass between an open proximal end of the guidewire tube and an open distal end, although in some designs side slits or other holes may be formed in the guidewire tube for passage of an associated guidewire.

The guidewire tube will be disposed within a balloon or other interventional or diagnostic element which is secured directly to the catheter body. Usually, the balloon will act to indirectly connect the guidewire tube to the catheter body, but in other instances, different bridging or connection structure could be provided. In the preferred case where the interventional element is an angioplasty or stent delivery balloon, the catheter body is usually connected to the proximal end of the guidewire tube by a sleeve or neck portion of the balloon which bridges the gap between the catheter body and the guidewire tube. In such cases, the proximal end of the guidewire tube may be deflected so that it passes radially outwardly through a portion of the balloon.

The catheters and structures of the present, however, are not limited to balloon angioplasty or other balloon catheter devices. Other interventional and diagnostic elements which might find use with the present invention include mechanically expandable elements, such as malecotts and expandable blades; ultrasonic transducers, including both intervention and imaging transducers; radiation sources, including both isotopic and electronic radiation sources (e.g. X-ray sources); drug release mechanisms; atherectomy assemblies; thermal detectors, such as those used for detecting vulnerable plaque; optical coherence tomography (OCT) elements; and the like.

In a first preferred embodiment of the present invention, a balloon catheter comprises a catheter body having a proximal end, a distal end, and a balloon inflation lumen extending to the distal end, usually from the proximal end. A balloon having a distal end and a proximal end is attached to the distal end of the catheter body. The balloon has a expandable region between the distal and proximal ends thereof. A guidewire tube is disposed within the balloon and has a proximal end and a distal end. The proximal end is spaced distally from the distal end of the catheter body and is not directly connected to the catheter body. In the specific embodiments, the guidewire tube is indirectly connected by a portion of the balloon which extends from the distal end of the catheter body and over the proximal portion of the guidewire tube.

Preferably, no portion of the catheter body will axially overlap with any portion of the guidewire tube. Usually, an axial gap of at least 1 mm will be maintained between the distal-most portion of the catheter body and the proximal-most portion of the guidewire tube, usually being at least 2 mm, often at least 3 mm, and sometimes 4 mm or more.

In the illustrated embodiments, the balloon has a distal neck portion, a proximal neck portion, and an expandable region therebetween. The proximal neck portion of the balloon may be joined over the distal end of the catheter body, may be joined under the distal end of the catheter body, or may be joined in a butt joint to the distal end of the catheter body.

In all these cases, the proximal end of the guidewire tube may open through either the neck portion of the balloon or the expandable region of the balloon. Usually, the proximal end of the guidewire tube will be deflected and sealed to a portion of the balloon. Alternatively, a hole may be formed in the side of the guidewire tube which is then connected directly or indirectly to the balloon to provide access into the guidewire lumen.

In further preferred constructions according to the present invention, the distal end of the guidewire tube will extend distally beyond the distal end of the balloon, typically by at least 1 mm, often by 5 mm, and sometimes by 10 mm or greater. Even more preferably, the distal end of the guidewire tube will be spaced distally from the distal end of the expandable region of the balloon by a distance which is greater than the distance of the proximal end of the guidewire tube and the proximal end of the expandable region of the balloon. Usually, the distal end of the guidewire tube is at least 1 cm from the distal end of the expandable region of the balloon, and the proximal end of the guidewire tube is no greater than 1 cm from the proximal end of the expandable region of the balloon. The length of the expandable region of the balloon, i.e. the distance between the distal and proximal ends of the expandable regions, is usually in the range from 1 cm to 5 cm. While these dimensions are typical, other embodiments of the invention may have dimensions which fall outside of these ranges.

In all cases, the proximal end of the guidewire tube is usually positioned within the proximal neck or other portion of the balloon so that the inflation medium from the inflation lumen of the catheter can pass by the guidewire tube and enter the expandable of the balloon. For example, at least a proximal portion of the guidewire tube may have a diameter which is less than that of the proximal neck portion of the expandable balloon. Alternatively, the guidewire may terminate within the expandable region of the balloon, thus leaving the proximal neck portion empty and free to pass inflation medium.

In other specific designs, a reinforcement collar or sheath may be placed over the proximal neck portion of the expandable balloon, typically spanning the transition between the balloon and the distal end of the catheter body. Such collar or sheath can provide stress relief for the junction between the catheter body and the balloon. Alternatively, a distal end of the catheter body may be chamfered or cut at an angle so that the portion of the body which extends furthest in the distal directional may help support the junction with the balloon, where the proximal end of the guidewire tube is deflected in parallel to the angle of the distal end of the guidewire tube.

All of the balloon catheter variations described above may be combined with a scoring or other external structure positioned over the balloon for the treatment of hardened or calcified plaque or other purposes. Typically, the scoring structure will comprise a plurality of helical scoring elements which are elastic so that they will radially expand when the balloon is inflated and radially close over the balloon when the balloon is deflated.

In a particular embodiment, the scoring structures will be attached at their proximal ends to the balloon catheter by an attachment structure. The attachment structure will have characteristics sufficient, such as size and compliance, to accommodate geometrical changes and reaction forces produced by the scoring structure as that structure is expanded by the balloon. Usually, the scoring structure will have a proximal end and a distal end, wherein the proximal end of the attachment structure is fixed to the catheter body and the distal end of the attachment structure is secured to the proximal end of the scoring structure. Usually, the distal end of the scoring structure is directly fixed to the catheter body such that the attachment structure axially extends to accommodate foreshortening of the scoring structure as the balloon is expanded. Preferably, the attachment structure will also rotationally deform to accommodate rotation of the scoring structure as the shell is expanded.

In particular embodiments, the attachment structure may comprise a compliance tube having an outer diameter and an inner diameter, where the tube extends over some portion of the outer surface of the catheter body. Usually, the inner diameter of the compliance tube is slightly larger than an outer diameter of the catheter body so that there is a clearance which permits the compliance tube to freely move with respect to the catheter body (other than at its attached proximal end) to permit both foreshortening and relative rotational motion as the scoring structure is expanded by the balloon. The length and other characteristics of the compliance balloon may be selected to control the compliance provided between the scoring structure and the catheter body, e.g. the compliance tube will have a wall thickness and/or a length which is/are selected to provide a desired compliance.

In other specific embodiments, the scoring or other external structure can be coated, impregnated, or otherwise coupled to or with a drug, nucleic acid, or other biologically active component that is to be delivered into the plaque, blood vessel wall, intimal layer, or elsewhere. By providing the biologically active agent on the external structure, the plaque or other lesion can be penetrated or otherwise breached by the structure to enhance delivery into or through the lesion. Particularly preferred is the delivery of anti-restenotic agents such as rapamycin, paclitaxel, and the various derivatives and analogs thereof which are now well described in the patent and medical literature.

BRIEF DESCRIPTION OF THE DRAWINGS

FIG. 2 is an enlarged view of a distal end of a first embodiment of the catheter of the present invention, shown in section.

FIG. 3 is an enlarged view of a second embodiment of a distal end of the catheter of the present invention, shown in section.

DETAILED DESCRIPTION OF THE INVENTION

Figure 1:
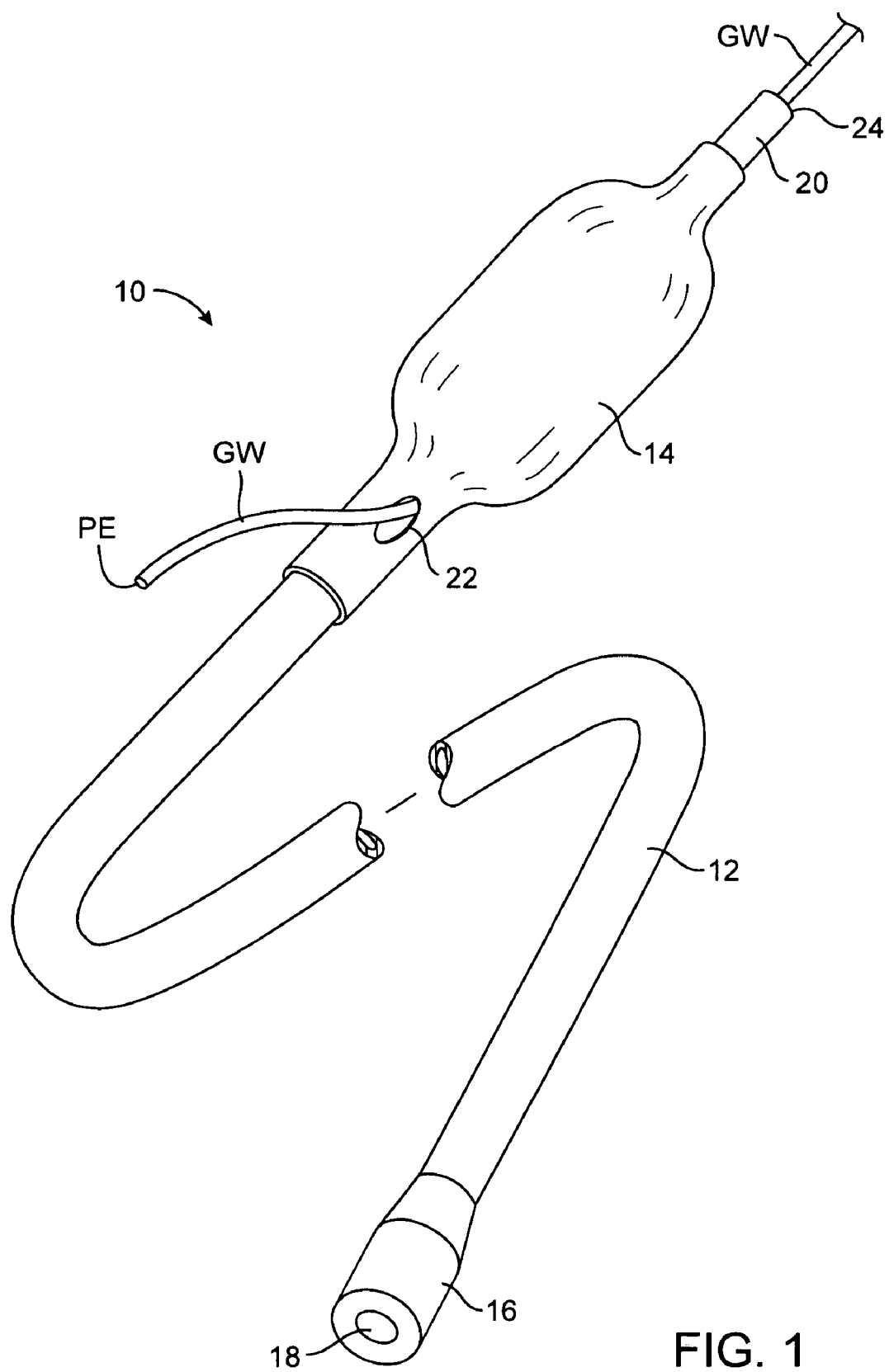
FIG. 1 is a perspective view of a facilitated guidewire exchange catheter constructed in accordance with the principles of the present invention.

Catheters according to the present invention will comprise a catheter body having a proximal end and a distal end, and an interventional or diagnostic element disposed at or near the distal end of the catheter body. As described above, the element will most often be an expandable balloon of the type which is used for performing angioplasty and/or for delivering stents, grafts, or other vascular prosthesis. Such balloons are well described in the patent and medical literature. In other instances, however, the element of the present invention can be any one of or a combination of the interventional or diagnostic elements listed above. All these listed elements are exemplary, the catheter of the present invention may comprise at least most of the interventional and diagnostic elements of the type which are used or which may be used in the future in interventional cardiology. Thus, the list provided above is intended to be exemplary, not exhaustive.

The catheter bodies of the present invention may also have a generally conventional structure. The catheter body will have a proximal end and a distal end with an expandable balloon or other interventional or diagnostic element mounted near the distal end. The dimensions, materials, and construction of the catheter body may vary widely and will depend on the particular application intended for the catheter. In the case of angioplasty and other intravascular coronary catheters, the catheter body will typically have a length in the range from 50 cm to 200 cm, usually in the range from 75 cm to 150 cm. The outside diameter of the catheter body will typically be in the range from 2 f-12 f. The ability to utilize a separate guidewire tube which extends distally beyond from the catheter body and which is not co-extensive with the catheter body is particularly advantageous for small-diameter catheters, typically having a diameter in the range from 2 Fr to 6 Fr. over at least their distal ends.

The catheter bodies of the present invention will usually be formed from nylon and pebax. Optionally, the catheter body or some portion thereof may be formed as a composite having a reinforcement material incorporated within a polymeric body in order to enhance strength, flexibility, and/or toughness. Suitable reinforcement layers include braiding, wire mesh layers, embedded axial wires, embedded helical or circumferential wires, and the like. As a further alternative, at least a proximal portion of the catheter body may in some instances be formed from super elastic other highly elastic hyprotube materials. The catheter body will include at least one continuous lumen extending from at or near its proximal end to at or near its distal end in order to provide for balloon inflation. While additional lumen(s) may be provided, there will typically be no lumens within the catheter body itself intended for receiving a guidewire. That is, the guidewire will be received only through the guidewire lumen in the guidewire tube, as described in detail below.

In exemplary embodiment of a balloon catheter, the balloon is at or near the distal end of the catheter may be formed separately or integrally with the body itself. Usually, the balloon will be extruded and formed in a separate step and later joined to the distal end of the catheter body in a conventional manner, e.g. by adhesives, heat fusing, ultrasonic welding, or some combination thereof. In some cases, however, it will be possible to form the balloon integrally, i.e., as a single extrusion, together with the catheter body, where the dimensions of the balloon may be imparted by heat expansion and setting in a non-matter. In either case, the interior of the balloon will be open to the continuous balloon inflation lumen of the catheter body. The guidewire tube will be present within the balloon but will be spaced distally from the distal end of the catheter body. In cases where the catheter body is formed separately from the balloon, the distal end of the catheter body will usually be the physical termination of the catheter body extrusion. In cases where the balloon is formed as a single extrusion with the catheter body (but later formed by heat expansion in setting) the distal end of the catheter body will considered the point at which the balloon material is thinned and begins to flare relative to the proximal catheter body.

The catheter will also typically include a proximal hub located at or near the proximal end of the catheter body. The hub will serve in a conventional manner to provide a luer or other fitting in order to connect the catheter to a source of balloon inflation, such as conventional angioplasty activation device. Unlike most angioplasty balloon catheter hubs, however, the hub of the present invention need not have any port or other provision for sealingly receiving a guidewire. The guidewire tube is provided within the inflatable balloon or other interventional or diagnostic element of the catheter. The guidewire tube will have dimensions and will be composed of a material which is compatible with the remainder of the balloon catheter construction. In particular, the material will be bondable to the balloon material and will have sufficient flexibility, durability, pushability, and the like in order to provide for proper performance. The material of the guidewire tube will be selected to provide an appropriate guidewire lumen material to permit advancement of the catheter over a conventional guidewire. Optionally, the guidewire lumen of the guidewire tube may be coated with a lubricous material in order to reduce friction. The length, diameter, and lumen diameter of the guidewire tube will be selected to be compatible with the catheter dimensions overall. Typically, the guidewire tube will a length in the range from 5 mm to 10 cm, typically from 5 mm to 7 cm. When utilized within an angioplasty or stent delivery balloon, the length of the guidewire tube will typically be 1 cm to 10 cm, and the outside diameter will typically be 2 Fr to 5 Fr.

391 Referring now to FIG. 1, an angioplasty balloon catheter 10 comprises a catheter body 12 having an inflatable balloon 14 at its distal end and a hub 16 at its proximal end. The hub includes a balloon inflation port 18, and a guidewire tube 20 is positioned within the balloon 14 and includes a proximal guidewire port 22 at its proximal end and a distal end guidewire port 24 at its distal end. The catheter 10 may thus be introduced over a conventional guidewire GW by passing the distal guidewire port 24 over the proximal end PE and advancing the catheter until the proximal end PE emerges from the proximal guidewire port 22, as shown in FIG. 1. The catheter may then be advanced through a patient's vasculature over the guidewire in a generally conventional manner. The relatively short engagement length of the guidewire within the guidewire tube 20 facilitates exchange of the catheter for a subsequent catheter.

The guidewire tube 20 may be positioned within the inflatable balloon 14 in a number of different ways, as illustrated in FIGS. 2-6. FIG. 2 illustrates guidewire generally as shown in FIG. 1. The balloon 14 is mounted over the distal end of catheter body 12 and secured by adhesives, heat bonding, ultrasonic bonding, or the like. In particular, the catheter body is secured within a proximal neck end 30 of the balloon which has an inner diameter generally corresponding to the outer diameter of the catheter body. Similarly, a distal neck portion 32 has an inner diameter generally corresponding to the outer diameter of the guidewire tube 20 and is attached thereto by adhesives, heat welding, ultrasonic welding, or the like. The proximal port 22 of the guidewire tube 20 is laterally deflected and terminates within a hole or passage in the proximal neck portion of the balloon 30. The guidewire tube 20 is not connected to the catheter body 12 in any way (other than indirectly by the proximal neck 30 of the balloon). That is, a gap G in the range from 0.1 mm to 2 cm may be left, typically being in the range from 1 mm to 5 mm. Similarly, the distal guidewire port 22 of the guidewire tube 20 will usually be closer to the expandable region 34 of the balloon 14 than is the proximal guidewire port 24. Usually, the proximal port 22 will be within a distance $d_2$ from the beginning of the expandable region 34 in the range from 0 mm to 1 cm, usually being from 0 mm to 5 mm. In contrast, the distal port 24 will be at a greater distance from the distal beginning of the expandable region 34, typically being at a distance $d_1$ in the range from 3 mm to 5 cm, typically from 5 mm to 3 cm, and often from 1 cm to 2 cm.

A first alternate construction for placement of the guidewire tube 120 within balloon 114 is illustrated in FIG. 3. In that instance, balloon 114 is received within the interior lumen of the catheter body 112 concealed thereto by adhesives, heat welding, ultrasonic welding, or the like. Proximal port 122 of the guidewire tube 120 is received within expandable region 134 of the balloon 114, rather than in the proximal neck portion 130 (as was the case in FIG. 2). Another difference is that distal guidewire port 124 terminates at the end of distal neck portion 132 of the balloon and does not extend therebeyond. Other aspects, however, may remain the same.

Figure 4:
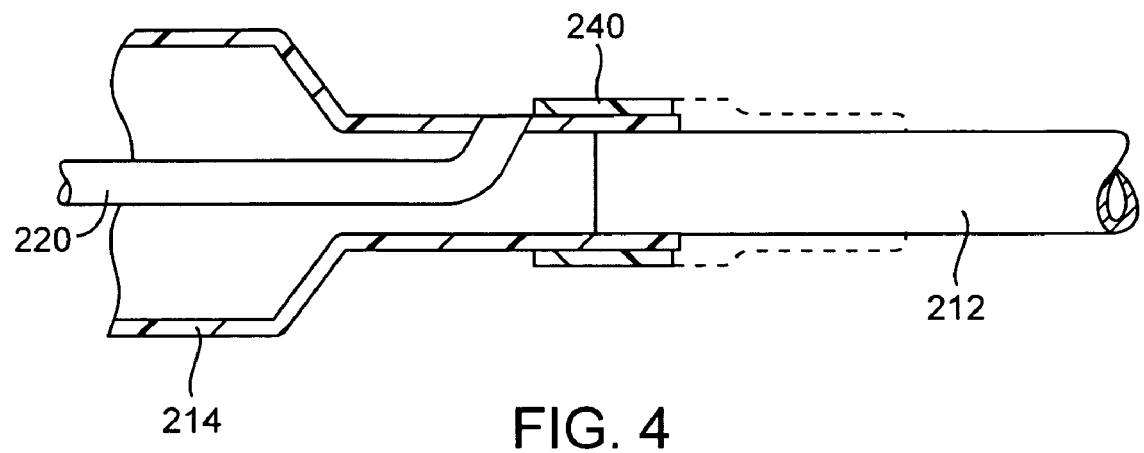
FIG. 4 is an enlarged view of a third embodiment of a distal end of the catheter of the present invention, shown in section.

As a further alternative construction, a sleeve 240 will be received over the junction between balloon 214 and catheter body 212, as shown in FIG. 4. The sleeve 240 may be formed over the location where the catheter body 212 terminates to provide stress relief. Optionally, the sleeve 240 may extend further proximally, as shown in broken line, in order to provide additional stress relief and help anchor the balloon to the catheter body.

Figure 5:
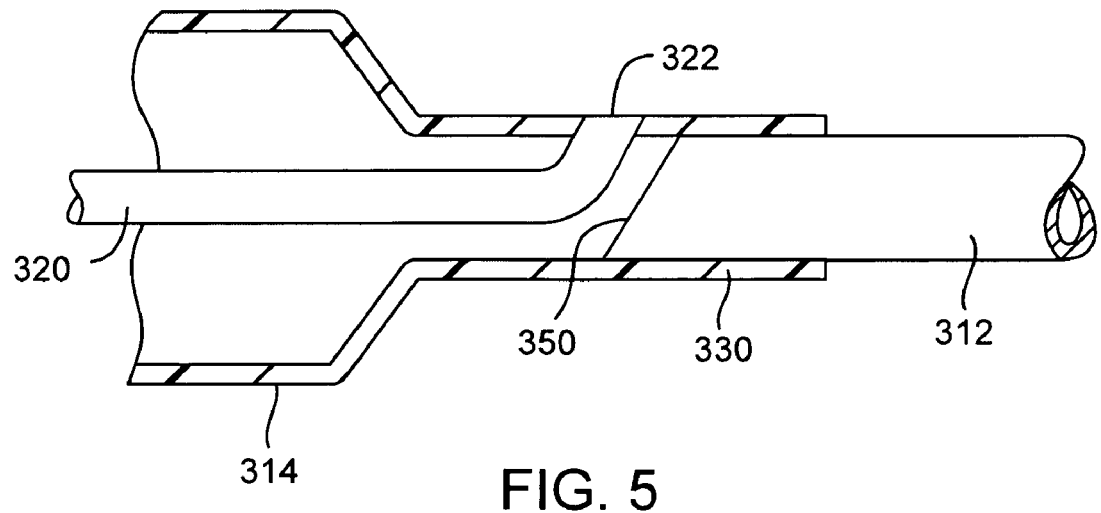
FIG. 5 is a fourth enlarged view of a distal end of the catheter of the present invention, shown in section.

In an still further optional construction, the distal end of the catheter body 312 may be chamfered, i.e., cut at an angle, as shown at 350 in FIG. 5. Such geometry allows a leading or distal-most end of the catheter body 312 to be positioned opposite from the distal guidewire port 322 of guidewire tube 320. This construction leaves the desired gap between the guidewire tube and the catheter body, but provides additional support and column strength for the structure as a whole.

Figure 6:
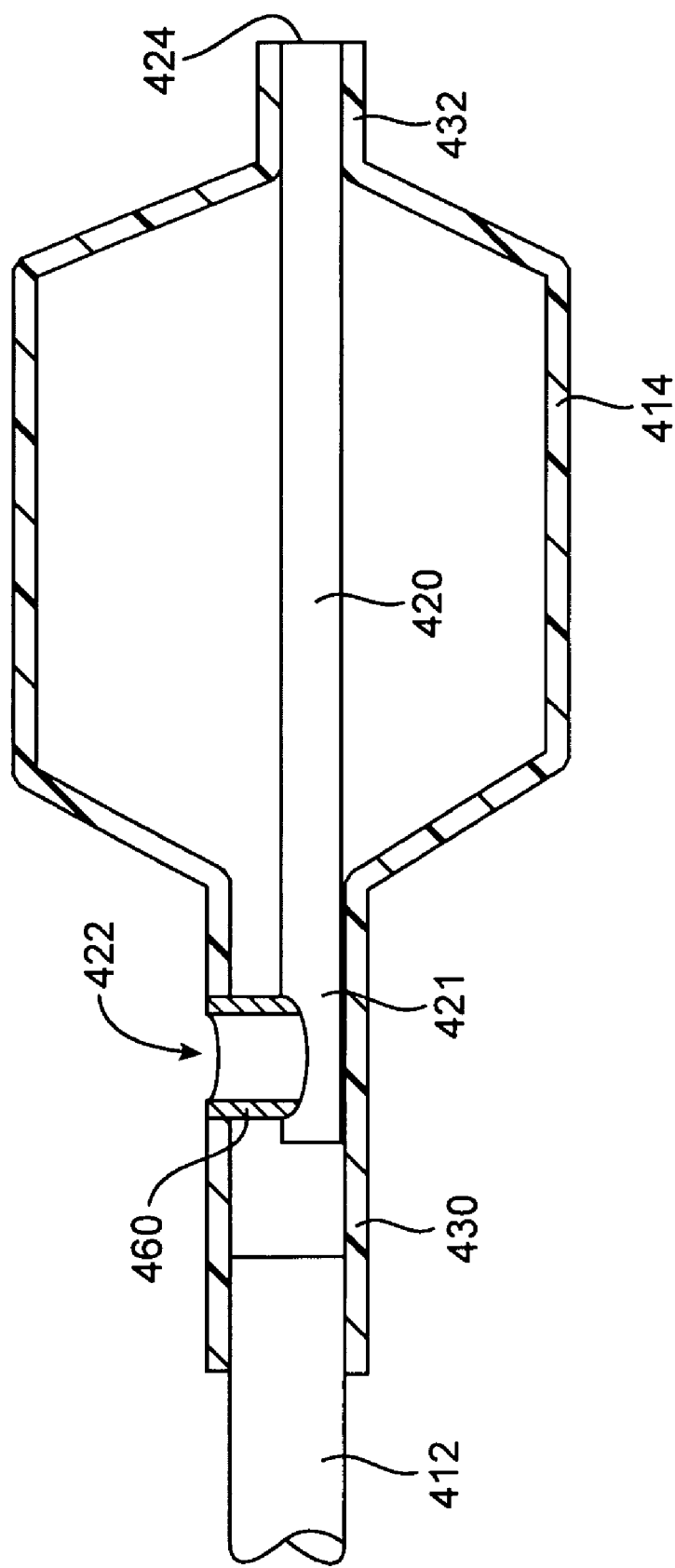
FIG. 6 is a fifth enlarged view of a distal end of the catheter of the present invention, shown in section.

As illustrated in FIG. 6, in a further alternative construction for guidewire tube 420 has a straight geometry. Guidewire tube 420 has a diameter which is generally less than that of the catheter body 412. Thus, the proximal portion 421 of the guidewire tube lies within the proximal neck 430 of the balloon 414, leaving a substantial gap available for introduction of an inflation medium. In order to connect the tube to a proximal guidewire port 422, a short tube or other connector 460 is provided. Alternatively, the connection could be provided by using an adhesive or other connecting material between the neck 430 and the aperture in the guidewire tube 420. Note that the proximal end of the guidewire tube 420 will be blocked to prevent loss of inflation medium through the guidewire lumen therein.

Figure 7:
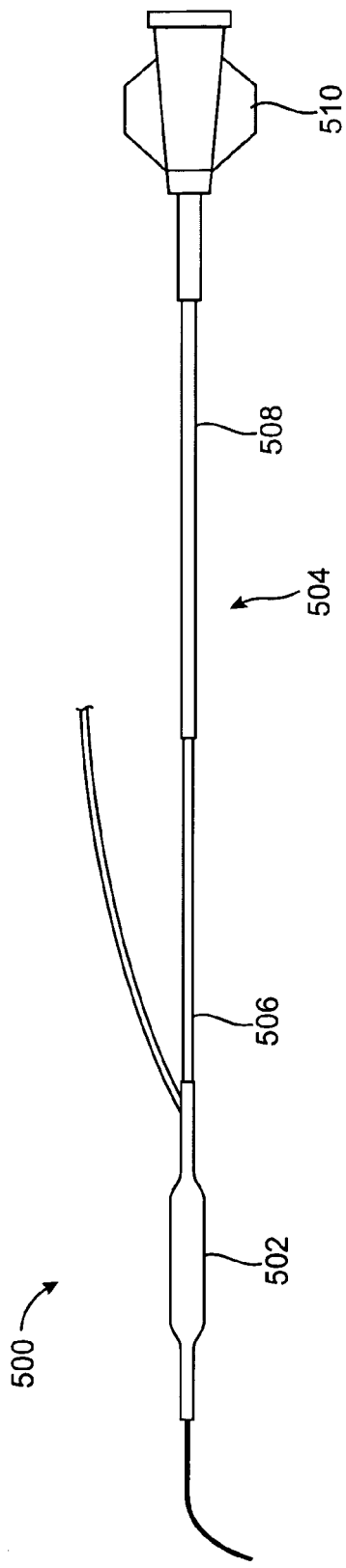
FIG. 7 illustrates a further exemplary embodiment of a balloon catheter constructed in accordance with the principles of the present invention.
Figure 8:
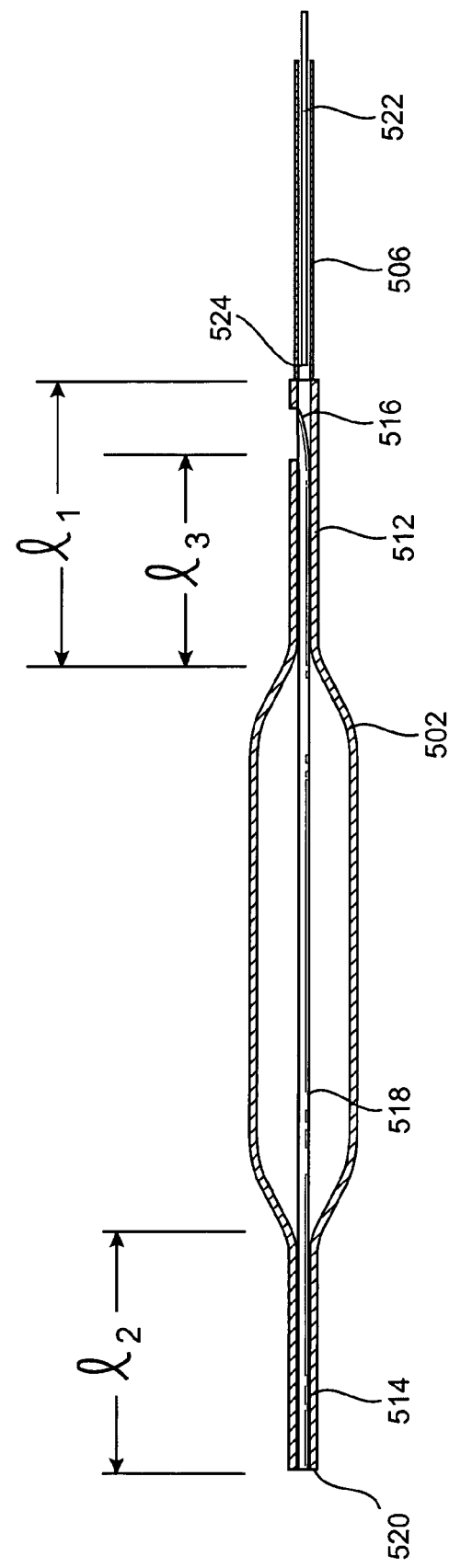
FIG. 8 is a detailed view of the distal end of the catheter of FIG. 7 shown in partial section.

An exemplary balloon catheter system 500 is illustrated in FIGS. 7 and 8. The catheter system 500 comprises a balloon structure 502 secured at the distal end of a catheter shaft 504 comprising a polymeric tube section 506 and a hypotube section 508. A proximal hub 510 is attached at the proximal end of the shaft 504 and provides a balloon inflation port.

As best shown in FIG. 8, the distal end of the polymeric tube portion 506 of the catheter shaft 504 is butt joined to the proximal end of the balloon structure 502. In particular, the polymeric tube 506 is joined to a non-inflatable section 512 of the balloon structure 502 having a length $l_1$ typically in the range from 0.5 cm to 2 cm, typically being no greater than 1 to 1.5 cm. The balloon structure 502 will also have a distal extension section 514 which extends beyond the distal end of the expandable region of the balloon by a length $l_2$ in the range from 0.7 cm to 3 cm, typically being at least 1 cm. The distance $l_2$ will typically exceed that of distance $l_3$ between the proximal end of the inflatable region of the balloon and a proximal guidewire port 516, as described in more detail below. The distance or length $l_3$ will usually be less than 1 cm and will preferably always be less than the length $l_2$.

The catheter 500 further includes a guidewire tube 518 which extends from a proximal guidewire port 516 to a distal guidewire port 520. The balloon 502 will typically be sealed to a distal region of the guidewire tube 520 but will not be sealed to the proximal portion of the guidewire tube. In this way, inflation medium introduced through the lumen of the catheter shaft (particularly through a continuous lumen formed through the hypotube 508 and polymeric tube 506). Preferably also, there will be no structure other than the non-inflatable section 512 of the balloon adjoining the distal end of the polymeric tube 506 and proximal end of the guidewire tube 516.

Preferred materials of construction for all polymeric components comprise nylon/PEBAX or other suitable polymers of the type conventionally employed in catheter construction. The particular material properties may be selected to provide desired stiffnesses, strengths, and other properties.

Optionally, all or a portion of the polymeric tube section 506 of the catheter shaft 504 may have a core wire 522 disposed in its lumen. The core wire will typically be composed of stainless steel and will provide a controlled or enhanced stiffness within the polymeric tube section extending from the hypotube section 508. A distal end 524 of the corewire 522 will typically terminate a short distance proximally of the proximal end of the non-inflatable section 512 of the balloon structure 502. In other embodiments, however, the core wire may extend to the distal end and/or into the non-inflatable section 512. In other embodiments, the core wire 522 is at least partially attached to the polymeric tube 506. One way to attach the core wire to the tube is using an adhesive, such as an adhesive that is cured by UV radiation once the core wire 522 is properly positioned in the polymeric tube 506. Curing could also be done by exposing the adhesive to other sources of energy, such as laser or RF or by heating the polymer tube until at least partial bonding is achieved.

Figure 9:
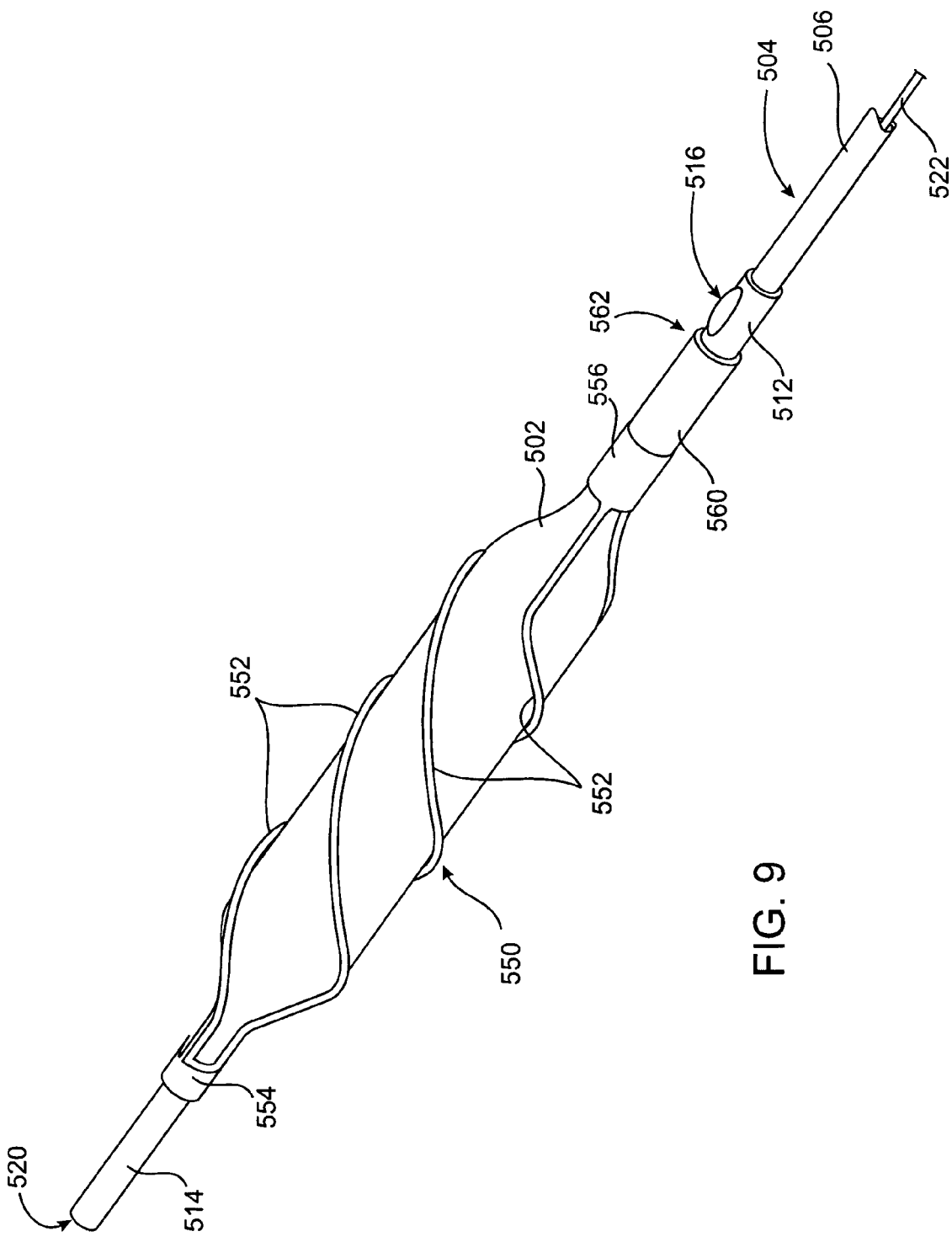
FIG. 9 is a perspective view of the distal end of the catheter of FIGS. 7 and 8, shown with a helical scoring structure in place.

Referring now to FIG. 9, the balloon catheters of the present invention are particularly suitable for delivering scoring structures and other external devices carried by the balloon. In particular, the balloon catheter system 500 can be adapted and used to deliver scoring structures comprising pluralities of helical scoring elements which radially expand when the balloon is inflated and which radially close over the balloon when the balloon is deflated. Specific designs for such helical scoring elements and other external balloon-carried devices are provided in commonly assigned, copending U.S. patent applications Ser. No. 10/631,499 (published as U.S. 2004/0143287); Ser. No. 10/810,330 (published as U.S. 2004/0243158); Ser. No. 10/917,917, filed on Aug. 13, 2004; Ser. No. 10/917,902, filed on Aug. 13, 2004; and Ser. No. 10/776,457, filed on Feb. 10, 2004, the full disclosures of each being incorporated herein by reference.

As illustrated in FIG. 9, the helical scoring structure 550 includes four helical elements 552 commonly attached at their distal ends to a distal collar 554 and at their proximal ends to a proximal collar 556. The distal collar 554 will usually be attached and immobilized with respect to the catheter, e.g. being directly attached to the guidewire tube 518 (not shown in FIG. 9) immediately distal to the distal end of the expandable region of the balloon 502.

The proximal collar 556, in contrast, will preferably be attached to a compliant tube 560 (or other suitable attachment structure as described in the copending applications incorporated by reference previously). The compliant tube 560, in turn, will be attached at or near its proximal end 562 to a proximal portion of the guidewire tube 518. The compliant tube will be sufficiently compliant or "elastic" so that it can accommodate the axial foreshortening and rotational "unwinding" of the helical scoring structure 550 as it is expanded by the balloon 502. In the embodiment of FIG. 9, the compliant tube 560 terminates distal to the proximal guidewire port 516. In other embodiments, however, the compliant tube could extend over the guidewire port so long as a sufficient aperture or passage is provided to allow the guidewire to extend through the guidewire port. In still other embodiments, the compliant tube could extend over and be attached directly to the catheter shaft 504 proximal to the attachment to the balloon 502.

The helical scoring structure 550 is illustrated in its expanded configuration in FIG. 9. That is, the balloon 502 is fully inflated to expand the individual helical element 552 radially outward with respect to the axis of the catheter. When the balloon is deflated, in contrast, the helical scoring structure 550 will elastically and radially close over the catheter structure, typically over the guidewire tube, to assume its low profile delivery configuration. Usually the individual helical elements 552 will be elastic with their normal or unstressed configuration being in the closed or low profile condition.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A balloon catheter comprising:
    a catheter body having a proximal end, a distal end, and a balloon inflation lumen extending to the distal end;
    a balloon having a distal end, a proximal end attached to the distal end of the catheter body, and an expandable region between the distal and proximal ends; and
    a guidewire tube disposed within the balloon and having a proximal end, a distal end, and a guidewire lumen therebetween, wherein the proximal end of the guidewire tube is spaced distally of the distal end of the catheter body, wherein the distal end of the guidewire tube is spaced-distally from the distal end of the expandable region of the balloon by a distance greater than the distance between the proximal end of the guidewire tube and the proximal end of the expandable region of the balloon.

2. A balloon catheter as in claim 1, wherein the distal end of the guidewire tube is at least 1 cm from the distal end of the expandable region of the balloon and the proximal end of the guidewire tube is no greater than 1 cm from the proximal end of the expandable region of the balloon.

3. A balloon catheter as in claim 2, wherein the length of the balloon between the distal and proximal expandable regions is from 1 cm to 5 cm.

4. A balloon catheter as in claim 1, wherein the balloon inflation lumen extends from the distal end to the proximal end of the catheter body.

5. A balloon catheter as in claim 1, wherein the balloon has a distal neck portion and a proximal neck portion, and wherein the expandable region is between said neck portions.

6. A balloon catheter as in claim 5, wherein the proximal neck portion of the balloon is joined over the distal end of the catheter body.

7. A balloon catheter as in claim 1, wherein the proximal neck portion of the balloon is joined under the distal end of the catheter body.

8. A balloon catheter as in claim 5, wherein the proximal neck portion of the balloon is butt joined to the distal end of the catheter.

9. A balloon catheter as in claim 1, wherein the proximal end of the guidewire tube opens through the expandable region of the balloon.

10. A balloon catheter as in claim 1, wherein the proximal end of the guidewire tube opens through the proximal neck portion of the balloon at a location distal of the proximal end of the catheter body.

11. A balloon catheter as in claim 10, wherein the proximal end of the guidewire tube is positioned within the proximal portion of the balloon so that inflation medium from the inflation lumen of the catheter body can pass the guidewire tube and enter the expandable region of the balloon.

12. A balloon catheter as in claim 1, wherein no portion of the catheter body overlaps axially with a portion of the guidewire tube.

13. A balloon catheter as in claim 12, wherein the gap between the catheter body and the guidewire tube is at least 1 mm.

14. A balloon catheter as in claim 1, further comprising a scoring structure over the balloon.

15. A balloon catheter as in claim 14, wherein the scoring structure comprises a plurality of helical scoring elements which are elastic to ideally expand when the balloon is inflated and to radially close over the balloon when the balloon is deflated.

16. A balloon catheter as in claim 15, further comprising an attachment structure having a proximal end and a distal end attached to the scoring structure, wherein the attachment structure is sufficiently sized and compliant to accommodate geometrical changes and reaction forces produced by the scoring structure as it is expanded by the balloon.

17. A catheter as in claim 16, wherein the scoring structure has a proximal end and a distal end, and wherein the proximal end of the attachment structure is fixed to the catheter body and the distal end of the attachment structure is secured to the proximal end of the scoring structure.

18. A catheter as in claim 17, wherein the distal end of the scoring structure is fixed to the catheter body, and wherein the attachment structure axially extends to accommodate foreshortening of the scoffing structure as the balloon is expanded.

19. A catheter as in claim 18, wherein the attachment structure rotationally deforms to accommodate rotation of the scoring structure as the shell is expanded.

20. A catheter as in claim 18, wherein the attachment structure comprises a compliance tube having an outer diameter and an inner diameter that extends over the catheter body.

21. A catheter as in claim 20, wherein the inner diameter of the compliance tube is larger than an outer diameter of the catheter body so that the compliance tube freely extends with respect to the catheter body as the external structure foreshortens.

22. A catheter as in claim 21, wherein the compliance tube inner diameter is sized so that the compliance tube freely rotates with respect to the catheter body as the scoring structure rotates.

23. A catheter as in claim 22, wherein the compliance tube is sized to control the compliance of the scoring structure and expansible shell.

24. A catheter as in claim 23, wherein the compliance tube has a wall thickness that is sized to control the compliance of the system.

25. A catheter as in claim 23, wherein the compliance tube has a length ranging from 1 cm to 10 cm.

26. An improved catheter of the type comprising a catheter body and an interventional or diagnostic element at a distal end of the catheter body, wherein the improvement comprises a guidewire tube passing through the interventional element wherein the guidewire tube has a proximal end which is spaced distally of a distal end of the catheter body by a distance less than that of a distal end of the guidewire tube from the interventional element.

27. An improved catheter as in claim 26, herein the interventional or diagnostic element is selected from the group consisting of balloons, mechanically expandable elements, ultrasonic transducers, radiation sources, heating sources, cryogenic sources, drug release mechanisms, atherectomy elements, thermal detectors, and optical coherence tomography (OCT) elements.

* * * * *